(12) United States Patent
Podtburg et al.

(10) Patent No.: US 7,795,000 B2
(45) Date of Patent: Sep. 14, 2010

(54) FOAMING COMPOSITION OF COMPETITIVE EXCLUSION MICROBES AND METHODS OF USING SAME

(75) Inventors: Teresa C. Podtburg, Waconia, MN (US); Bruce Schmidt, Apple Valley, MN (US); Bruce Cords, Inver Grove Heights, MN (US); Lawrence A. Grab, Dusseldorf (DE); David A. Halsrud, Minneapolis, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 11/233,922

(22) Filed: Sep. 22, 2005

(65) Prior Publication Data

US 2006/0067915 A1    Mar. 30, 2006

Related U.S. Application Data

(60) Provisional application No. 60/612,882, filed on Sep. 24, 2004.

(51) Int. Cl.
*C12N 1/34* (2006.01)
*C12N 1/20* (2006.01)

(52) U.S. Cl. ............... 435/246; 435/252.4; 435/252.9; 435/853

(58) Field of Classification Search ............ 435/246
See application file for complete search history.

(56) References Cited

U.S. PATENT DOCUMENTS

| | | | |
|---|---|---|---|
| 3,929,678 A | 12/1975 | Laughlin et al. | |
| 4,243,543 A * | 1/1981 | Guilbert et al. | 510/234 |
| 4,525,351 A * | 6/1985 | Gehrman et al. | 424/535 |
| 4,565,647 A * | 1/1986 | Llenado | 516/14 |
| 4,904,273 A | 2/1990 | Lauchenauer | |
| 4,923,981 A * | 5/1990 | Weibel et al. | 536/56 |
| 5,082,682 A | 1/1992 | Peterson | 426/564 |
| 5,182,100 A * | 1/1993 | Klueppel et al. | 424/49 |
| 5,232,849 A | 8/1993 | Vedamuthu et al. | |
| 5,269,959 A * | 12/1993 | Schreibman | 510/372 |
| 5,374,433 A | 12/1994 | Bowling et al. | |
| 5,576,035 A | 11/1996 | Bowling et al. | |
| 5,817,362 A | 10/1998 | Vandenbergh et al. | |
| 5,972,673 A | 10/1999 | Moineau et al. | |
| 5,980,969 A * | 11/1999 | Mordini et al. | 426/597 |
| 6,022,568 A * | 2/2000 | Lesens et al. | 426/61 |
| 6,036,952 A * | 3/2000 | Oh | 424/93.1 |
| 6,039,984 A * | 3/2000 | Bowling et al. | 426/61 |
| 6,053,364 A | 4/2000 | van der Heijden | |
| 6,110,372 A | 8/2000 | Perriello | |
| D452,653 S | 1/2002 | Boshuizen et al. | |
| D452,822 S | 1/2002 | Boshuizen et al. | |
| D456,260 S | 4/2002 | Boshuizen et al. | |
| 6,376,696 B1 | 4/2002 | Raab et al. | |
| 6,387,874 B1 * | 5/2002 | Schalitz et al. | 510/530 |
| 2003/0109405 A1 | 6/2003 | Kellar et al. | |
| 2006/0073129 A1 * | 4/2006 | Doyle et al. | 424/93.45 |

FOREIGN PATENT DOCUMENTS

| | | |
|---|---|---|
| EP | 0 705 843 A1 | 4/1996 |
| EP | 0 809 612 B1 | 3/2000 |
| EP | 1 231 280 A1 | 8/2002 |
| GB | 1 585 874 | 3/1981 |
| WO | WO 95/06663 | 3/1995 |
| WO | WO 01/50866 A2 | 7/2001 |
| WO | WO 2004/048597 A2 | 6/2004 |

OTHER PUBLICATIONS

Anderson F.A. "Amended final report on the safety of cocamide DEA". Journal of the American College of Toxicology. 1966, 15(6), pp. 527-542.*
Zhao et al. Abstracts of the General Meeting of the American Society for Microbiology. 2003, vol. 103, pp. P-011, abstract.*
Heron et al. Journal of Applied Bacteriology. 1993, vol. 75, No. 1, pp. 13-17, abstract.*
Zhao et al. "Control of Listeria monocytogenes in a biofilm by competitive exclusion microorganisms". Applied and Environmental Microbiology. Jul. 2004, vol. 70, No. 7, pp. 3996-4003.*
Harkonen et al. Water Science and Technology. 1999, 39 (7), 219-225.*
Andersen F.A. Journal of the American College of Toxicology. 1996. 15(6):527-542.*
Atlas R. Handbook of Microbiological media. 1994, p. 933-934.*
Zhao et al. Abstracts of the General Meeting of the American Society for Microbiology. 2003, vol. 103, pp. P-011.*
Parente et al. "A comparison of factors affecting the production of two bacteriocins from lactic bacteria". Journal of Applied Bacteriology. 1992, 73, 290-298.*
Murray et al. Journal of Micribiological Methods. 2008, 75:325-328.*
Food Ingredients First: Nutrition, Ingredients and Foods Online—Newsmaker, "Patents for products with potential as natural antimicrobial agents," http://www.foodingredientsfirst.com/newsmaker_article.asp?idNewsMaker=3157&fSite=..., 2 pages (Mar. 28, 2003).
Wagner, R. et al., "Phenotypic and genotypic characterization of competitive exclusion products for use in poultry," *Journal of Applied Microbiology*, vol. 94, No. 6, p. 1098 (1 page abstract) (Jun. 2003).

\* cited by examiner

*Primary Examiner*—Vera Afremova
(74) *Attorney, Agent, or Firm*—Merchant & Gould P.C.

(57) ABSTRACT

The present invention relates to a composition including a microbial component and a foaming component, wherein the composition can be used to prevent the proliferation, or otherwise competitively exclude the continued growth of, undesirable microbes. The present invention also includes a method of using this composition.

9 Claims, 1 Drawing Sheet

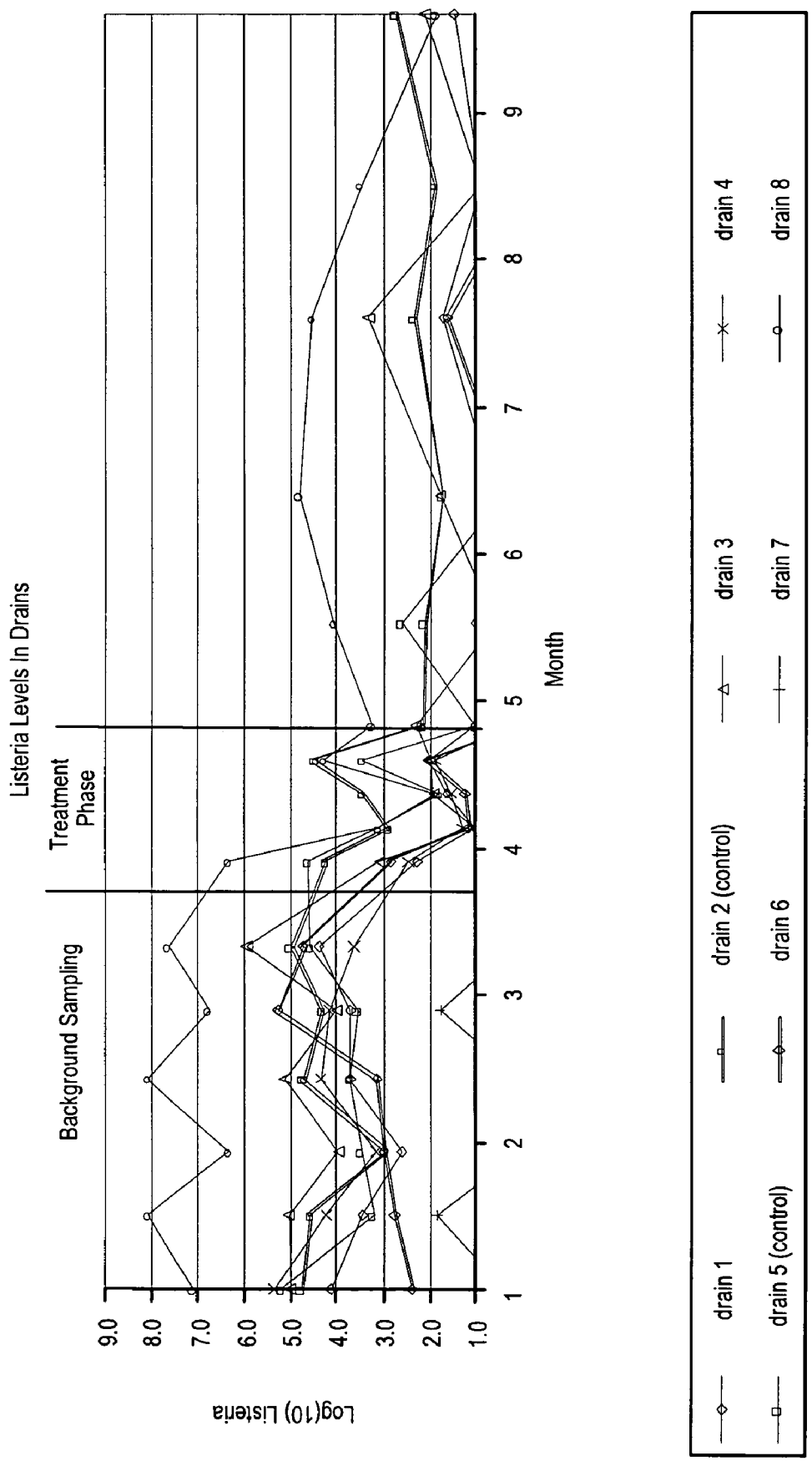

US 7,795,000 B2

FOAMING COMPOSITION OF COMPETITIVE EXCLUSION MICROBES AND METHODS OF USING SAME

This application claims priority of U.S. Patent Application No. 60/612,882 filed Sep. 24, 2004, which application is incorporated herein by reference.

FIELD OF THE INVENTION

The present invention relates to a composition including a microbial component and a foaming component, wherein the composition can be used to prevent the proliferation, or otherwise competitively exclude the continued growth of, undesirable microbes. The present invention also includes a method of using this composition.

BACKGROUND OF THE INVENTION

Undesirable microbes, for instance, bacteria such as *Escherichia coli, Salmonella, Listeria monocytogenes*, and *Staphylococcus aureus*, can be pathogenic for humans. Foods containing such bacteria can cause serious illness to humans. Certain microbes can also have an adverse affect on the organoleptic and/or aesthetic properties of food products. Of course, there are many other environments in which undesirable bacteria are present, and which present hazards or problems that could be ameliorated if the growth and proliferation of such undesirable bacteria could be inhibited. Accordingly, there is a need for reducing the growth, proliferation, or survival of such undesirable microbes.

Conventional application of anti-microbial agents aims to eliminate nearly all unwanted bacteria. However, bacteria are ubiquitous, and it has proven very difficult to maintain a product or surface with sufficiently low levels of unwanted bacteria for an extended period of time. Accordingly, there is a need for a method that protects against the growth, proliferation, or survival of undesirable microbes for a prolonged period of time.

SUMMARY OF THE INVENTION

The present invention relates to a composition including a microbial component and a foaming component, wherein the composition can be used to prevent the proliferation, or otherwise competitively exclude the continued growth of, undesirable microbes. The present invention also includes a method of using this composition.

In an embodiment, the invention includes a composition of a microbe. Such a composition can include a foaming component and a microbial component. The foaming component can include at least one of surfactant and protein. The surfactant can include at least one of nonionic surfactant, anionic surfactant, and amphoteric surfactant. The composition can be in the form of a use composition (ready to be foamed) or a foamed composition. The use composition can include about 0.01 to about 1 wt-% of foaming component and about 0.05 to about 5 wt-% of microbial component. The composition can be provided as a two part composition.

The present invention also includes methods of using the microbe composition. The method can include reducing the population of an undesirable microbe on an object. Such a method can include contacting the object with a foam composition comprising competitive exclusion microbe. The object can be a drain. The method can include applying a competitive exclusion microbe. Such a method can include foaming a composition comprising the competitive exclusion microbe. Foaming can employ any of a variety of foaming apparatus, such as a portable foamer or an aspirating wall mounted foamer.

BRIEF DESCRIPTION OF THE DRAWING

The FIGURE shows *Listeria* levels in drains as discussed in the Applying Compositions to Drains Example.

DETAILED DESCRIPTION OF THE INVENTION

Definitions

As used herein, the term "microorganism" refers to any noncellular or unicellular (including colonial) microbe. Microorganisms include all prokaryotes. Microorganisms include bacteria (including cyanobacteria and Mycobacteria), lichens, microfungi, protozoa, virinos, viroids, viruses, fungi (e.g., molds and yeast), and some algae. As used herein, the term "microbe" is synonymous with microorganism.

As used herein, the term "undesirable microbe" refers to any microbe that exhibits, introduces, or causes an undesirable attribute or effect on a surface, facility, or object. Undesirable microbes include pathogenic microbes and spoilage microbes.

As used herein, the terms "pathogenic microbe" and "microbial pathogen" refer to microbes that are believed to induce adverse health affects in living species, such as humans, or otherwise render such species more susceptible to disease, infection, or some other malady. Pathogenic microbes can cause illness or disease either directly or indirectly, e.g. through the production of by-products. Depending upon the context in which such microbes are present, pathogenic microbes can include, for example: *Escherichia coli, Salmonella, Listeria* (e.g., *Listeria monocytogenes*), *Staphylococcus, Streptococcus, Bacillus anthracis, Campylobacter coli, Campylobacter jejuni, Francisella tularensis, Sarcocystis, Toxoplasma gondil, Yersinia enterocolitica, Yersinia pseudotuberculosis, Brucella, Chlamydia petechia, Leptospira*, and *Clostridium*.

As used herein, the term "spoilage microbe" refers to microbes, such as bacteria, yeast, or molds, that can alter the organoleptic or aesthetic properties of perishable products, such as foods, meats, etc., or reduce the ability of the perishable product to serve its intended function, such as nourishment. Spoilage microbes can introduce or cause such undesirable properties in a variety of fashions. For instance, spoilage microbes can create undesirable by-products that can alter the taste, smell, or color of a product. In addition, spoilage bacteria can metabolize desirable compounds, thereby undesirably altering the organoleptic or aesthetic properties of a product. Depending upon the context in which such microbes are present, spoilage microbes can include, for example, bacteria from the genera *Pseudomonades, Lactobacillus*, and *Enterobacter*; molds from the genera *Aspergillus* and *Penicillium*; and yeasts from the genera *Saccharomyces* and *Candida*.

As used herein, the term, "benign microbe" refers to any microbe that does not introduce or exhibit undesirable characteristics or properties, either directly or indirectly. The class of benign microbes excludes undesirable microbes such as pathogenic or spoilage microbes. Benign microbes include microbes that have been genetically modified, or otherwise altered, to eliminate or significantly reduce the undesirable characteristic(s). Different microbes may be benign for one purpose and not benign for another. Accordingly, as used herein, the term benign should be considered in context with the purpose for which the composition is used. The term "innocuous microbes" refers to a subclass of benign microbes, specifically microbes that do not pose a health risk for humans.

As used herein, the terms "competitively exclude" and "competitive exclusion" refer to a process by which the composition of the present invention can reduce the growth or proliferation of, or even kill, undesirable microbes. The process of competitive exclusion can occur in a number of manners. The rapid proliferation of a first microbe to the extent that it reduces, or even eliminates, the ability of a second microbe to grow, proliferate, and/or survive, constitutes one form of competitive exclusion. This form of competitive exclusion will be referred to as "passive competitive exclusion."

A second form of competitive exclusion involves the production of by-products by a first microbe. The by-products can reduce, or even eliminate, the ability of a second microbe to grow, proliferate, and/or survive. This form of competitive exclusion will be referred to as "active competitive exclusion." Both forms of competitive exclusion can be used under the present invention, either in combination or alone.

For the purpose of this patent application, successful reduction of a population of a microbe is achieved when the populations of the microbe is reduced by at least about 0.3 $\log_{10}$, for example at least about 0.3-1 $\log_{10}$. Any increased reduction in population of microbes is an added benefit that provides higher levels of protection.

As used herein, the term "object" refers to something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include surfaces and articles employed in hospitality and industrial sectors.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing, blancher cleaning, food packaging materials, cutting boards, beverage chillers and warmers, meat chilling or scalding equipment, cooling towers, food processing garment areas (including drains).

As used herein, weight percent (wt-%), percent by weight, % by weight, and the like are synonyms that refer to the concentration of a substance as the weight of that substance divided by the weight of the composition and multiplied by 100.

Amounts of ingredients stated in this patent application generally refer to the amount of the particular active ingredient (e.g., nonionic surfactant). Amounts stated for commercial products typically relate to the amount of the commercial product. The amount of active provided by the commercial product can be determined from the concentration of the commercial product and the fraction of the commercial product that is the active ingredient.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use compositions in the real world; through inadvertent error in these procedures; through differences in the manufacture, source, or purity of the ingredients employed to make the compositions or carry out the methods; and the like. Whether or not modified by the term "about", it is intended that the claims include equivalents to the quantities.

Foaming Microbial Composition

The present invention relates to a foaming microbial composition and methods employing it. The present composition can be in the form of a liquid, a solid, a gel, or any other suitable form that can be capable of forming a foam, for example, for application. The present invention also relates to the microbial composition in the form of a foam, the foamed microbial composition.

In an embodiment, the present composition includes a microbial component and a foaming component. The microbial component can include any microbe that it might be desirable to include in a foaming composition. For example, the microbial component can include a benign microbe or an innocuous microbe, either of which can be a competitive exclusion microbe. The microbial component can include a microbe that can reduce the growth or proliferation of an undesirable microbe, such as a pathogenic microbe or spoilage microbe.

The foaming component can include any agent suitable for forming a foam, such as a surfactant, a protein, a foam booster, a polymer, or the like. In an embodiment, the foaming component can include an agent suitable for forming a foam and maintaining an adequate level of viability of a microbe in the microbial component. The foaming component can include anionic, nonionic, and/or amphoteric surfactant. In an embodiment, the foaming component can be a surfactant other than a cationic surfactant (e.g., a quaternary ammonium surfactant). Certain cationic surfactants are antimicrobial agents. In an embodiment, the foaming component does not kill or inactivate a microbe present in the microbial component.

In an embodiment, the microbial component and the foaming component are selected to maintain viability of the microbe for a sufficient time for the microbe to provide a benefit after application. For example, in a composition or method employed for competitive exclusion, the microbe can grow for a period of time or to an extent sufficient to allow it to reduce the population of or to competitively exclude an undesirable microbe. Accordingly, in an embodiment, the microbe can survive in the foamed composition for at least about 2 hours. In an embodiment, the microbe can survive for at least about 2 hours after application of the present composition to an object.

The foaming composition can also include foam boosting agent, source of alkalinity, sequestrant, or any of various other additives. In an embodiment, certain additional ingredients can be selected to maintain the ability of the microbial component to grow and to competitively exclude an undesirable microbe.

The present invention also includes a method employing the foaming microbial composition. Applying the present composition can include foaming the composition onto an object. For example, the present method can include applying to an object the foaming microbial composition and competitively excluding one or more undesirable microbes. Competitively excluding undesirable microbes can include growth or reproduction of the microbe in the foaming microbial composition to an extent that it reduces the population of undesirable microbe. For example, the present composition can reduce the proliferation, or otherwise competitively exclude the continued growth, of an undesirable microbe.

The present method can include reducing the growth or proliferation of an undesirable microbe, such as a pathogenic microbe or a spoilage microbe. For example, the composition can be employed in a method for competitively excluding, or inhibiting, proliferation or growth of a pathogenic microbe or a spoilage microbe on an object or surface in a food processing plant. Of course, the composition of the present composition and method can be employed for reducing the population of other kinds of undesirable microbes in other environments.

Although not limiting to the present invention, it is believed that employing the present foaming composition can provide advantageous efficacy of the microbial component. It is believed that the foaming composition can retain an effective concentration of the microbial component at the site of action for a longer time than a liquid composition. For example, in an embodiment, it is believed that the foaming composition can, by benefit of being a foam, remain positioned on the surface or object being treated, even if the surface is vertical. Thus, it is believed that prolonged retention of the microbes on the object can provide a larger population of the microbes of the microbial component, which can provide enhanced competitive exclusion of an undesirable microbe.

Further, although not limiting to the present invention, it is believed that the foaming composition can allow the microbial component to obtain better dispersion and/or penetration on the surface that is being treated. For example, foaming action can work the composition into cracks, holes, threads (e.g., pipe threads), or other small openings or imperfections in an object.

Microbial Component

The present composition can include a microbial component. The microbial component can include any microbe that can be included in a foaming composition. The microbe can be any microbe that might grow on a surface to which it can be applied. In an embodiment, the microbe is selected to competitively exclude or to reduce the population of an undesirable microbe on the surface. For example, the microbial component can include a benign microbe or an innocuous microbe. The microbial component can include a plurality of different benign microbes. The microbial component can include a plurality of different innocuous microbes. In an embodiment, the microbe can reduce the population of a pathogenic microbe or a spoilage microbe.

In an embodiment, the microbe can grow and proliferate in the foamed composition and/or on the surface of an object. Suitable microbes (e.g., benign microbes) include facultative, sacrophilic, gram positive bacteria. Suitable microbes include bacteria from the genera *Enterococcus, Lactococcus, Lactobacillus, Hafnia*, mixtures thereof, or the like. Such microbes can be benign microbes. In an embodiment, the microbe can include *Enterococcus durans, Lactococcus lactis, Lactobacillus plantarum, Lactobacillus delbrueckii, Lactobacillus leichmannii, Lactobacillus jensenii, Lactobacillus bulgaricus, Lactobacillus helveticus, Lactobacillus acidophilus, Hafnia alvei*, mixtures thereof, or the like. Such microbes can be benign microbes. The microbe can include *Enterococcus durans* 152 having ATCC accession number PTA-4758, *Enterococcus durans* 141-1 having ATCC accession number PTA-4759, *Lactococcus lactis* C-1-92 having ATCC accession number PTA-4760, *Lactococcus lactis* C-1-152 having ATCC accession number PTA-4761, mixtures thereof, or the like.

The microbe can be an obligately homofermentive bacteria. The microbe can be a facultatively homofermentive bacteria. Either of these types of bacteria can be a benign microbe.

In an embodiment, the microbe can include a plurality of different types of bacteria. For instance, the combination of *Hafnia alvei* with *Lactobacillus delbrueckii* has been found advantageous in certain systems. While not intending to be bound by theory, it is believed that *Hafnia alvei* bacteria may initially colonize on the surface being treated and provide an environment suitable for the proliferation of *Lactobacillus delbrueckii*.

In an embodiment, the microbial component can include any microbe suitable for replacing an undesirable microbe. For example, when the undesirable microbe is a pathogenic microbe, the microbial component can include a spoilage microbe. For example, when the undesirable microbe is a pathogenic microbe, the microbial component can include a microbe less harmful or pathogenic than the undesirable microbe. For example, *Pseudomonas* could be considered less harmful or pathogenic than *Listeria* in certain industries.

In an embodiment, the microbial component (and/or at the foaming component) can be selected to maintain viable microbes upon treatment with the foaming mechanism. For example, the foaming mechanism can be a physical foaming mechanism or a chemical foaming mechanism, or both, depending upon the formulation and method of application used for the composition. The microbial component can be selected to provide an adequate number of viable microbes after either physical or chemical foaming.

In an embodiment, the microbial component can be selected for competitive exclusion. For example, the microbial component can be selected for passive competitive exclusion. Such a passive competitive exclusion process can employ benign or innocuous microbes that can thrive on the object being treated. It is believed that such thriving growth can competitively exclude an undesirable microbe. For example, the microbial component can be selected for active competitive exclusion. Such an active competitive exclusion process can employ benign or innocuous microbes that can thrive on the object being treated. Such an active competitive exclusion process can employ benign or innocuous microbes selected to produce by-products that reduce, or even eliminate, the ability of undesirable microbes to grow, reproduce, and/or survive. The microbial component can be selected to provide active competitive exclusion, passive competitive exclusion, or both active and passive competitive exclusion.

The microbial component can also include any of a variety of substances suitable for stabilizing, storing, or maintaining the microbe. For example, the microbial component can also include culture medium, buffer, nutrient, or the like. The microbial component can be provided as a solid or liquid separate from the foaming component. That is, the microbial component can be part of a 2-part system. Alternatively, the microbial component can be provided with additional components of the foaming composition, such as the foaming component, but separate from other components, such as a source of alkalinity, an enzyme, sequestrant, or the like. That is, the microbial component can be part of a 2-part system in which the foaming component is provided in the same part as the microbial component. Any portion of the foaming composition that can adversely affect the microbe can be supplied as a part of a 2-part system separate from the microbial component.

In an embodiment, the microbial component or the microbe is selected to maintain viability of the microbe for a sufficient time for the microbe to provide a benefit after application of the foaming composition. For example, for competitive exclusion, the microbe can grow for a period of time or to an extent sufficient for reducing the population of or for competitively excluding an undesirable microbe. In an embodiment, the microbe can survive in the foamed composition for at least about 2 hours. In an embodiment, the microbe can survive for at least about 2 hours after application of the present composition to an object. In an embodiment, the microbe can survive in the foamed composition for at least about 3 hours. In an embodiment, the microbe can survive for at least about 3 hours after application of the present composition to an object. In an embodiment, the microbe can survive in the foamed composition for at least about 5 hours. In an embodiment, the microbe can survive for at least about 5 hours after application of the present composition to an object. In an embodiment, the microbe can survive in the foamed composition for at least about 8 hours. In an embodiment, the microbe can survive for at least about 8 hours after application of the present composition to an object. The survival time can relate to survival under ambient conditions in a structure that can also be occupied by humans.

The composition of the present invention can contain a sufficient amount of the microbial component in order to allow the growth and proliferation of the microbe. Accordingly, the composition should include at least about $10^3$ colony forming units (CFU)/ml, about $10^5$ CFU/ml, or up to about $10^{12}$ CFU/ml.

Foaming Component

In an embodiment, the present composition includes a foaming component. The foaming component can include any agent suitable for forming a foam, such as a surfactant, a protein, a foam booster, a polymer, or the like.

In an embodiment, the foaming component can include an agent suitable for forming a foam and maintaining an adequate level of viability of a microbe in the microbial component. In an embodiment, the foaming component is selected to maintain viability of the microbe for a sufficient time for the microbe to provide a benefit after application. For example, the foaming component can be selected to provide an environment in which the microbe can grow for a period of time or to an extent sufficient to allow it to reduce the population of or to competitively exclude an undesirable microbe. Accordingly, in an embodiment, the microbe can survive in the foamed composition for at least about 2 hours. In an embodiment, the microbe can survive for at least about 2 hours after foaming the present composition on to an object. In an embodiment, the microbe can survive in the foamed composition for at least about 3 hours. In an embodiment, the microbe can survive for at least about 3 hours after foaming the present composition on to an object. In an embodiment, the microbe can survive in the foamed composition for at least about 5 hours. In an embodiment, the microbe can survive for at least about 5 hours after foaming the present composition on to an object. In an embodiment, the microbe can survive in the foamed composition for at least about 8 hours. In an embodiment, the microbe can survive for at least about 8 hours after foaming the present composition on to an object. The survival time can relate to survival under ambient conditions in a structure that can also be occupied by humans.

The foaming component can also include any of a variety of substances suitable for stabilizing the microbe in a foam. The foaming component can be provided as a solid or liquid separate from the microbial component. That is, the foaming component can be part of a 2-part system. Alternatively, the foaming component as a mixture also including the microbial component, but separate from other components, such as a source of alkalinity, an enzyme, sequestrant, or the like. That is, the foaming component can be part of a 2-part system in which the foaming component is provided in the same part as the microbial component.

Surfactant

The foaming component of the present foaming composition can include a surfactant or surfactant blend. A variety of surfactants can be used in the present composition, including anionic, nonionic, and amphoteric surfactants that are commercially available. The foaming component should not adversely affect the growth or proliferation of the microbial component or otherwise inhibit competitive exclusion of undesirable microbes. Accordingly, the surfactant or surfactant blend can be provided substantially, or entirely free from antimicrobial agents. Anionic and nonionic surfactants are employed in certain embodiments. For a discussion of surfactants, see Kirk-Othmer, *Encyclopedia of Chemical Technology*, Third Edition, volume 8, pages 900-912.

In an embodiment, the present composition can include surfactant at about 1 to about 50 wt-%, about 2 to about 30 wt-%, or about 5 to about 20 wt-%. These percentages can refer to percentages of the commercially available surfactant composition, which can contain solvents, dyes, odorants, and the like in addition to the actual surfactant. In this case, the percentage of the actual surfactant chemical can be less than the percentages listed. These percentages can refer to the percentage of the actual surfactant chemical. Surfactant can be present at any of these amounts not as part of a range and/or at any of these amounts not modified by about. In an embodiment, the foaming composition includes surfactant in an amount effective to provide a desired level of foaming.

A ready to use or use composition according to the present invention can include surfactant at about 0.003 to about 5 wt-%, about 0.01 to about 0.3 wt-%, about 0.03 to about 5 wt-%, about 0.1 to about 3 wt-%, about 0.3 to about 5 wt-%, or about 1 to about 5 wt-%. The surfactant can be present at any of these amounts not as part of a range and/or at any of these amounts not modified by about.

In an embodiment, the surfactant includes anionic surfactant, amphoteric surfactant, nonionic surfactant, or mixture thereof. In an embodiment, the surfactant includes a nonionic surfactant. In an embodiment, the surfactant includes an anionic surfactant. In an embodiment, the anionic surfactant includes alkyl sulfonate, alkylaryl sulfonate, alcohol alkoxylate carboxylate, sarcosinate, taurate, acyl amino acid, alkanoic ester, phosphate ester, sulfuric acid ester, salt or ester thereof, or mixture thereof. In an embodiment, the surfactant includes amphoteric surfactant. In an embodiment, the amphoteric surfactant includes acyl amino acid, N-alkyl amino acid, salt or ester thereof, or mixture thereof.

In an embodiment, the present composition includes about 0.1 to about 3 wt-% nonionic surfactant and about 1 to about 40 wt-% anionic surfactant, about 0.2 to about 2 wt-% nonionic surfactant and about 2 to about 20 wt-% anionic surfactant, or about 0.3 to about 1 wt-% nonionic surfactant and about 5 to about 15 wt-% anionic surfactant. The composition can include any of these ranges or amounts not modified by about. In an embodiment, the present composition includes nonionic surfactant (e.g., amine oxide surfactant) and anionic surfactant (e.g., alkyl or alkylaryl carboxylate, sulfate or sulfonate surfactant).

Nonionic Surfactant Nonionic surfactants useful in the invention are generally characterized by the presence of an organic hydrophobic group and an organic hydrophilic group. Certain nonionic surfactants can be produced by the condensation of an organic aliphatic, alkyl aromatic, fatty alcohol, or polyoxyalkylene hydrophobic compound with a hydrophilic alkaline oxide moiety, which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Nonionic surfactants useful in the present compositions, include those having a polyalkylene oxide polymer as a portion of the surfactant molecule. Such nonionic surfactants include, for example, sorbitan and sucrose esters and their ethoxylates; alkoxylated ethylene diamine; alcohol alkoxylates such as alcohol ethoxylate propoxylates, alcohol propoxylates, alcohol propoxylate ethoxylate propoxylates, alcohol ethoxylate butoxylates, fatty alcohol ethoxylates (e.g., tridecyl alcohol alkoxylate, ethylene oxide adduct), and the like; nonylphenol ethoxylate, polyoxyethylene glycol ethers, and the like; carboxylic acid esters such as glycerol esters, polyoxyethylene esters, ethoxylated and glycol esters of fatty acids, and the like; carboxylic amides such as diethanolamine condensates, monoalkanolamine condensates, polyoxyethylene fatty acid amides, and the like; polyalkylene oxide block copolymers including an ethylene oxide/propylene oxide block copolymer such as those commercially available under the trademark PLURONIC (BASF-Wyandotte), and the like; ethoxylated amines and ether amines commercially available from Tomah Corporation; polyalkylene oxide free nonionics such as alkyl polyglycosides; and other like nonionic compounds. Silicone surfactants such as the ABIL B8852 (Goldschmidt) can also be used.

Suitable nonionic surfactants include alkyl phenol ethoxylates, linear and secondary alcohol ethoxylates (fatty alcohol ethoxylates, e.g., tridecyl alcohol alkoxylate, ethylene oxide adduct), ethoxy/propoxy block surfactants, and polyether siloxanes. Examples of suitable nonionic surfactants include EO/PO block nonionic surfactant terminated in PO, silicone nonionic surfactant, benzyl ether of a polyethoxylated primary alcohol, nonylphenol ethoxylate (e.g., nonylphenol 9.5 mole ethoxylate), amine oxides, and the like.

Suitable nonionic surfactants include nonionic block copolymers, alcohol alkoxylates, ethylene oxide-propylene oxide copolymers, alkyl polyglycosides, alkanolamides, and mixtures thereof. Suitable alcohol alkoxylates include alcohol ethoxylates, alcohol propoxylates, alkyl phenol ethoxylate-propoxylates, and mixtures thereof.

Useful nonionic surfactants in the present invention include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp.

Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from about 1,000 to about 4,000. Ethylene oxide is then added to sandwich this hydrophobe between hydrophilic groups, controlled by length to constitute from about 10% by weight to about 80% by weight of the final molecule.

Tetronic® compounds are tetra-functional block copolymers derived from the sequential addition of propylene oxide and ethylene oxide to ethylenediamine. The molecular weight of the propylene oxide hydrotype ranges from about 500 to about 7,000; and, the hydrophile, ethylene oxide, is added to constitute from about 10% by weight to about 80% by weight of the molecule.

Suitable nonionic block copolymer surfactants also include polyoxyethylene-polyoxypropylene block copolymers. Suitable polyoxyethylene-polyoxypropylene block copolymers that can be used have the formulae:

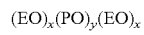

wherein EO represents an ethylene oxide group, PO represents a propylene oxide group, and x and y reflect the average molecular proportion of each alkylene oxide monomer in the overall block copolymer composition. Preferably, x is from about 10 to about 130, y is about 15 to about 70, and x plus y is about 25 to about 200. It should be understood that each x and y in a molecule can be different. The total polyoxyethylene component of the block copolymer is preferably at least about 20 mol-% of the block copolymer and more preferably at least about 30 mol-% of the block copolymer. The material preferably has a molecular weight greater than about 1,500 and more preferably greater than about 2,000.

Although the suitable polyoxyethylene-polyoxypropylene block copolymer structures provided above have 3 blocks and 5 blocks, it should be appreciated that the nonionic block copolymer surfactants according to the invention can include more or less than 3 and 5 blocks. In addition, the nonionic block copolymer surfactants can include additional repeating units such as butylene oxide repeating units. Furthermore, the nonionic block copolymer surfactants that can be used according to the invention can be characterized heteric polyoxyethylene-polyoxypropylene block copolymers. Suitable surfactants that can be used according to the invention are available from BASF under the name Pluronic, and a suitable EO-PO co-polymer that can be used according to the invention is available under the name Pluronic N3.

2. Condensation products of one mole of alkyl phenol wherein the alkyl chain, of straight chain or branched chain configuration, or of single or dual alkyl constituent, contains from about 8 to about 18 carbon atoms with from about 3 to about 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from about 6 to about 24 carbon atoms with from about 2 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co., Tomahdol manufactured by Tomah[3] Products, and Alfonic® manufactured by Vista Chemical Co.

The alcohol alkoxylate surfactants that can be used according to the invention can have the formula:

$$R(AO)_x\text{—}X$$

wherein R is an alkyl group containing 6 to 24 carbon atoms, AO is an alkylene oxide group containing 2 to 12 carbon atoms, x is 1 to 20, and X is hydrogen or an alkyl or aryl group containing 1-12 carbon atoms. The alkylene oxide group is preferably ethylene oxide, propylene oxide, butylene oxide, or mixture thereof.

4. Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

5. Polyhydroxy fatty acid amide surfactants suitable for use in the present compositions include those having the structural formula $R^2CONR^1Z$ in which: R1 is H, $C_1$-$C_4$ hydrocarbyl, 2-hydroxy ethyl, 2-hydroxy propyl, ethoxy, propoxy group, or a mixture thereof, $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

6. The alkyl ethoxylate condensation products of aliphatic alcohols with from 0 to about 25 moles of ethylene oxide are suitable for use in the present compositions. The alkyl chain of the aliphatic alcohol can either be straight or branched, primary or secondary, and generally contains from 6 to 22 carbon atoms.

7. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_8$-$C_{18}$ ethoxylated fatty alcohols with a degree of ethoxylation of from 3 to 50.

8. Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

The alkyl polyglycoside surfactants that can be used according to the invention can have the formula:

$$(G)_x\text{-O—R}$$

wherein G is a moiety derived from reducing saccharide containing 5 or 6 carbon atoms, e.g., pentose or hexose, R is a fatty aliphatic group containing 6 to 24 carbon atoms, and x is the degree of polymerization (DP) of the polyglycoside representing the number of monosaccharide repeating units in the polyglycoside. The value of x can be between about 0.5 and about 10. R can contain 10-16 carbon atoms and x can be 0.5 to 3.

9. Fatty acid amide surfactants suitable for use the present compositions include those having the formula: $R^6CON(R^7)_2$ in which $R^6$ is an alkyl group containing from 7 to 21 carbon atoms and each $R^7$ is independently hydrogen, $C_1$-$C_4$ alkyl, $C_1$-$C_4$ hydroxyalkyl, or —$(C_2H_4O)_xH$, where x is in the range of from 1 to 3.

Alkanolamides that can be used as nonionic surfactants include alkanolamides having the following formula:

$$R_1\text{—}\overset{\text{O}}{\underset{\|}{C}}\text{—}\overset{R_2}{\underset{|}{N}}\text{—}R_3$$

wherein $R_1$ is $C_6$-$C_{20}$ alkyl group, $R_2$ is hydrogen or a $C_1$-$C_3$, and $R_3$ is hydrogen or a $C_1$-$C_3$ alkyl group. A suitable alkanolamide is available as cocodiethanolamide.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Semi-Polar Nonionic Surfactants

The semi-polar type of nonionic surface active agents are another class of nonionic surfactant useful in compositions of the present invention. Generally, semi-polar nonionics are high foamers and foam stabilizers, which can limit their application in CIP systems. However, within compositional embodiments of this invention designed for high foam methodology, semi-polar nonionics would have immediate utility. The semi-polar nonionic surfactants include the amine oxides, phosphine oxides, sulfoxides and their alkoxylated derivatives.

10. Amine oxides are tertiary amine oxides corresponding to the general formula:

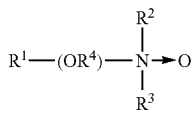

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the octyl, coconut, or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis (2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

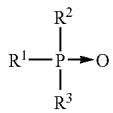

wherein the arrow is a conventional representation of a semi-polar bond; and, $R^1$ is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis (hydroxymethyl)tetradecylphosphine oxide.

Semi-polar nonionic surfactants useful herein also include the water soluble sulfoxide compounds which have the structure:

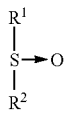

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Suitable semi-polar nonionic surfactants for the compositions of the invention include dimethyl amine oxides, such as decyl dimethyl amine oxide, lauryl dimethyl amine oxide, myristyl dimethyl amine oxide, cetyl dimethyl amine oxide, combinations thereof, and the like.

In an embodiment, the present foaming composition includes amine oxide surfactant at about 1 to about 50 wt-%, about 2 to about 30 wt-%, or about 5 to about 20 wt-%. In an embodiment, the present foaming composition includes amine oxide surfactant at about 10 wt-%. In an embodiment, the present foaming composition includes about 0.1 to about 3 wt-% amine oxide surfactant, about 0.2 to about 2 wt-% amine oxide surfactant, or about 0.3 to about 1 wt-% amine oxide surfactant. In an embodiment, the present foaming composition includes amine oxide surfactant at about 0.5 (e.g., 0.6) wt-%. The composition can include any of these ranges or amounts not modified by about. In an embodiment, the foaming composition includes surfactant in an amount effective to provide a desired level of foaming.

In an embodiment, the present composition includes amine oxide surfactant as a particular proportion of the foaming surfactant blend. For example, the foaming surfactant blend can include 0.5 to 2 parts by weight amine oxide surfactant in each 10 to 20 parts by weight of the blend. For example, the foaming surfactant blend can include 1 part by weight amine oxide surfactant in each 10-15 parts by weight of the blend.

Anionic Surfactants

Also useful in the present invention are surface active substances which are categorized as anionics because the charge on the molecule is negative; or surfactants in which the molecule carries no charge unless the pH is elevated to neutrality or above (e.g. carboxylic acids). Polar (hydrophilic) solubilizing groups found in anionic surfactants include carboxylate, sulfonate, sulfate, phosphate, and the like. Among cations (counter ions) associated with these polar groups, sodium, lithium and potassium can impart water solubility; ammonium and substituted ammonium ions can provide both water and oil solubility; and, calcium, barium, and magnesium can promote oil solubility.

It is known that anionics are excellent detersive surfactants and can have high foam profiles. Further, anionic surface active compounds can be employed to impart special chemical or physical properties other than detergency to the composition. Anionics can be employed as gelling agents or as part of a gelling or thickening system. Anionics are excellent solubilizers and can be used for hydrotropic effect and cloud point control. Anionic surfactants that can be used according to the invention include any anionic surfactant available in the cleaning industry.

The majority of large volume commercial anionic surfactants can be subdivided into several chemical classes and additional sub-groups known to those of skill in the art and described in "Surfactant Encyclopedia", *Cosmetics & Toiletries*, Vol. 104 (2) 71-86 (1989). Anionic surfactants useful in the present compositions, include, for example, carboxylates such as alkylcarboxylates (carboxylic acid salts) and polyalkoxycarboxylates, alcohol ethoxylate carboxylates, nonylphenol ethoxylate carboxylates, ester carboxylic acids (e.g. alkyl succinates), ether carboxylic acids, and the like; sulfonates such as alkylsulfonates, alkylaryl sulfonates (e.g., alkylbenzenesulfonates, such as linear dodecyl benzene sulfonic acid or salts thereof), alkylarylsulfonates, sulfonated fatty acid esters, isethionates (e.g. acyl isethionates), and the like; sulfates such as sulfated alcohols, sulfated alcohol ethoxylates, sulfated alkylphenols, alkylsulfates, sulfosuccinates, alkylether sulfates, and the like; phosphate esters such as alkylphosphate esters, ethoxylated alcohol phosphate esters, and the like; and acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionics include sodium alkylarylsulfonate, alkylbenzenesulfonates (e.g., linear dodecyl benzene sulfonic acid or salts thereof), sodium alkyl sulfate (e.g., sodium lauryl sulfate), ethoxylated alcohol phosphate esters, alpha-olefin sulfonate, carboxylates such as alkylcarboxylates (carboxylic acid salts), and fatty alcohol sulfates. Suitable anionic surfactants include carboxylates, isethionates, sulfonates and sulfates.

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside (the nonionic nonsulfated compounds being described herein).

Suitable alkyl ether sulfates that can be used in the foaming composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether ethoxylate sulfate and is available under the name Steol CS-460.

Suitable alkyl sulfates that can be used in the foaming composition include those having an alkyl group containing 6 to 24 carbon atoms. Suitable alkyl sulfates include sodium lauryl sulfate and sodium lauryl/myristyl sulfate.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids.

Suitable anionic surfactants include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the foaming composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the foaming composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the foaming composition include those having an alkyl group containing 6 to 24 carbon atoms.

Suitable alpha olefin sulfonates that can be used in the foaming composition include those having alpha olefin groups containing 6 to 24 carbon atoms.

Anionic carboxylate surfactants suitable for use in the present compositions include the alkyl ethoxy carboxylates, the alkyl polyethoxy polycarboxylate surfactants and the soaps (e.g. alkyl carboxyls). Secondary soap surfactants (e.g. alkyl carboxyl surfactants) useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary soap surfactants typically contain no ether linkages, no ester linkages and no hydroxyl groups. Further, they typically lack nitrogen atoms in the head-group (amphiphilic portion). Suitable alkylcarboxylates include those with 6 to 16 carbons, 8 to 16 carbons, 7 to 11 carbons, e.g., 8, 9, 10, 11, or 12 carbons. In an embodiment, the alkylcarboxylate includes isononanoic acid.

Other anionic detergents suitable for use in the present compositions include olefin sulfonates, such as long chain alkene sulfonates, long chain hydroxyalkane sulfonates or mixtures of alkenesulfonates and hydroxyalkane-sulfonates. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule.

The particular salts will be suitably selected depending upon the particular formulation and the needs therein. The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

In an embodiment, the present foaming composition includes anionic surfactant at about 1 to about 50 wt-%, about 2 to about 30 wt-%, or about 5 to about 20 wt-%. The composition can include any of these ranges or amounts not modified by about. In an embodiment, the foaming composition includes surfactant in an amount effective to provide a desired level of foaming.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at column 23, line 58 through column 29, line 23.

Amphoteric Surfactants

Amphoteric, or ampholytic, surfactants contain both a basic and an acidic hydrophilic group and an organic hydrophobic group. These ionic entities may be any of anionic or cationic groups known for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge. Suitable amphoteric surfactants include betaines, amine oxides, sultaines, amphoacetates, imidazoline derivatives, and mixtures thereof.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants can be subdivided into two major known classes such as those described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention can have the following general formulae:

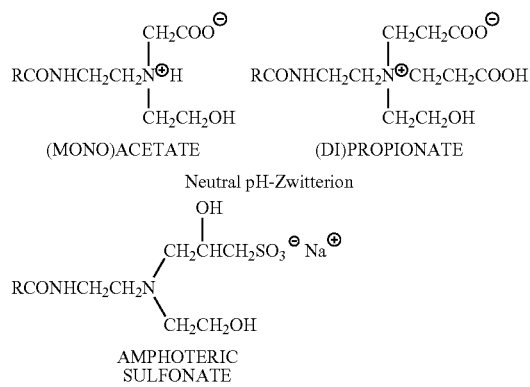

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Suitable amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8$-$C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In these R is preferably an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. For example, these coconut derived surfactants can include as part of their structure an ethylenediamine moiety, an alkanolamide moiety, an amino acid moiety (e.g., glycine), or a combination thereof; and an aliphatic substituent of from about 8 to 18 (e.g., 12) carbon atoms. Such a surfactant can also be considered an alkyl amphodicarboxylic acid. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Miranol™ C2M-SF Conc., also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Suitable zwitterionic surfactants include β-N-alkylaminopropionates, N-alkyl-β-iminodipropionates, imidazoline carboxylates, N-alkylbetaines, sulfobetaines, sultaines, amine oxides and polybetaine polysiloxanes. Betaine and sultaine surfactants are suitable zwitterionic surfactants for use herein.

A general formula for these compounds is:

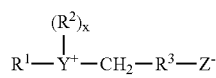

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

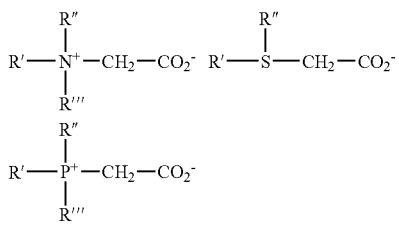

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

Suitable polybetaine polysiloxanes have the formula:

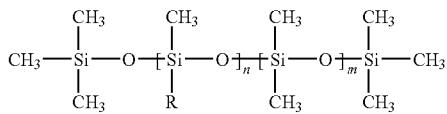

wherein R is

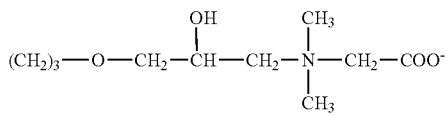

n is 1 to 100 and m is 0 to 100, preferably 1 to 100. Preferred polybetaine polysiloxanes are available under the name ABIL® from Goldschmidt Chemical Corp. Preferred amine oxides that can be used include alkyl dimethyl amine oxides containing alkyl groups containing 6 to 24 carbon atoms. A suitable amine oxide is lauryl dimethylamine oxide.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the composition of the present invention includes a betaine. For example, the composition can include cocoamidopropyl betaine. The betaine can be present in the composition at about 0.01 to about 30 wt-%, about 0.05 to about 20 wt-%, or about 0.1 to about 10 wt-%.

Foam Boosting Agent

The present foaming composition can also include a foam boosting agent, such as foam boosting surfactant, foam boosting solvent, or mixtures thereof. The foam booster, in combination with the surfactant or other surfactant, is provided to assist foaming, which refers to facilitating the maintenance of a foam that can be generated from a use solution containing a concentrate composition of the invention. Such a foam may be applied to a food or beverage packaging environment. Any foam booster that is compatible with the surfaces being treated and the surfaces that contact the treated surfaces may be used.

Foam Boosting Surfactant

Foam boosting surfactants suitable for use in the composition of the invention include, for example, amides, betaines, sultaines, amine oxides, and the like. Suitable amides are known in the art and include, for example, diethanol coconut amide. Suitable betaines are known in the art and include, for example, alkyl betaine (e.g., coco dimethyl betaine), alkyl amidopropyl betaine (e.g., lauramidopropyl betaine, coco/oleamidopropyl betaine, and oleamidopropyl betaine), etc. Suitable sultaines are known in the art and include, for example, alkyl amidopropyl sultaines and alkyl ether sultaines. Suitable amine oxides are known in the art and include, for example, lauryl amine oxide. In an embodiment, the foam boosting surfactant includes an amide such as diethanol coconut amide or amine oxide.

The composition can contain enough foam booster to provide a desirable amount of foam (e.g., to maintain a desirable contact time, to facilitate adherence to a vertical surface, or to allow for visual examination of a use solution applied to a food or beverage environment). A desirable amount of foam includes an amount that does not completely break down for at least 2 minutes, preferably 3.5 minutes, and more preferably 5 minutes. But the amount of foam booster should not exceed an amount that would cause the concentrate to become too viscous to be pumped or dispensed. The concentrate composition of the invention can include about 1 weight percent to about 5 weight percent, preferably about 2 weight percent to about 4 weight percent, and more preferably about 2 weight percent to about 3 weight percent of active foam booster.

Foam Boosting Solvent

A solvent that assists in the generation of a foam can be referred to as a 'foam-boosting solvent". For example, in a composition including a low concentration of surfactant, a foam-boosting solvent can assist in the generation of a desired foam when processed through a foamer. The foam boosting agent can be any foam booster that does not adversely affect the growth or proliferation of the microbial component of the composition, or otherwise adversely affect the competitive exclusion of undesirable microbes.

Certain types of solvents that have been found to function as foam-boosting solvents can be characterized in several ways. For example, foam-boosting solvents that have assisted in the generation of a foam can be characterized as having an HLB (hydrophilic-lipophilic balance) value of at least about 6.9 and an OHLB (organic hydrophilic-lipophilic balance) value of between about 12 and about 20. HLB is a measure of water miscibility with values of 7.3 or greater corresponding to complete water solubility. OHLB values refer to the partitioning ability between water and organic phase with higher OHLB values corresponding to a greater tendency to partition into the organic phase. HLB values and OHLB values for solvents are readily available for most solvents. Suitable foam-boosting solvents that can be used according to the invention can also be characterized as having a vapor pressure at room temperature of less than about 5 mmHg. The vapor pressure at room temperature can be less than about 1 mmHg, and can be less than about 0.1 mmHg. In addition, it may be desirable to provide the foam-boosting solvent as one characterized as GRAS (generally recognized as safe) by the FDA for direct or indirect food additives.

Suitable foam-boosting solvents include glycols, glycol ethers, derivatives of glycol ethers, and mixtures thereof. Suitable glycols include those having at least four carbon atoms such as hexylene glycol. Suitable glycol ethers include alkylene glycol ethers and aromatic glycol ethers. Suitable glycol ethers include those having the formula:

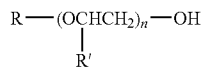

wherein R is a $C_1$-$C_6$ aliphatic or aromatic group, R' is H, $CH_3$, or $C_2H_5$, and n has a value of at least 1. The value of n can be between about 1 and about 4, and can be between about 1 and about 3. A suitable glycol ether includes dipropylene glycol methyl ether wherein R is $CH_3$, R' is $CH_3$, and n has a value of 2. Another suitable glycol ether is diethylene glycol butyl ether (sometimes referred to as butyl carbitol) wherein R is $C_4H_9$, R' is H, and n has a value of 2. A suitable aromatic glycol ether is ethylene glycol phenyl ether where R is a phenyl group, R' is H, and n is a value of 1. Other suitable glycol ethers include $C_1$-$C_6$ alkylene glycol ethers such as propylene glycol butyl ether, dipropylene glycol propyl ether, ethylene glycol butyl ether, diethylene glycol propyl ether, and triethylene glycol methyl ether. Suitable glycol ethers are commercially available under the name Dowanol® from the Dow Chemical Company. For example, n-propoxypropanol is available under the name Dowanol PnP.

Suitable derivatives of glycol ethers include those glycol ethers modified to include an additional group or functionality such as an ester group. Suitable derivatives of glycol ethers include those having the following formula:

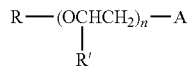

wherein R is a $C_1$-$C_6$ aliphatic or aromatic group, R' is H, $CH_3$, or $C_2H_5$, n has a value of at least 1, and A is an ester, amide, or ether group. The value of n can be between about 1 and about 4, and can be between about 1 and about 3. A suitable derivative of a glycol ether includes propylene glycol methyl ether acetate. It should be understood that certain glycol ethers and derivatives such as ethylene glycol phenyl ether can be used with additional solvents for coupling.

The composition can include an amount of the foam-boosting solvent to provide a desired foam when processed through a foamer (e.g., a mechanical foaming head). It has been found that the amount of foam-boosting solvent that can be provided to assist in the generation of a foam can be provided in an amount that does not significantly decrease the viscosity of the composition prior to foaming. That is, the amount of the foam-boosting solvent can be provided so that the composition that includes the foam-boosting solvent has a viscosity that is within about 50 centipoise of an otherwise identical composition except not including the foam-boosting solvent when the viscosity is measured on a Brookfield viscometer, model DV-E, at 22° C. a spindle speed of 100 rpm and a number 4 spindle, or at a spindle and speed that provides for measurement of viscosity.

It is expected that the foam-boosting solvent will be present in the composition in an amount of at least about 0.1 wt-%, and can be included in an amount up to about 5 wt-%. A suitable range of foam-boosting solvent in the composition is between about 0.5 wt-% and about 3 wt-%. Another suitable range of the foam-boosting solvent is between about 1 wt-% and about 2 wt-%.

It is believed that the foam-boosting solvent can be provided in a composition containing a relatively low concentration of surfactant to help assist in the generation of a foam when processed through a mechanical foaming head. The amount of the foam-boosting solvent can be provided based upon the amount of total surfactant in the composition. For example, when the total amount of surfactant is relatively low, it is desirable to provide enough foam-boosting solvent so that the composition generates a foam when processed through a mechanical foaming head. A suitable low concentration of total surfactant is about 0.05 wt-%. It is expected that at total surfactant concentrations of about 0.05 wt-% to about 10 wt-%, the foam-boosting solvent can be provided at a concentration of about 0.1 wt-% to about 5 wt-%, a concentration of between about 0.5 wt-% and about 3 wt-%, and a concentration of between about 1 wt-% and about 2 wt-%.

Sequestrant

The present foaming composition can include sequestrant, builder, or chelator. In general, a sequestrant is a molecule capable of coordinating (i.e., binding) the metal ions commonly found in natural water to prevent the metal ions from interfering with the action of the other ingredients of the foaming composition. Some chelating/sequestering agents can also function as a threshold agent when included in an effective amount. For a further discussion of chelating agents/sequestrants, see Kirk-Othmer, *Encyclopedia of Chemical Technology*, Third Edition, volume 5, pages 339-366 and volume 23, pages 319-320.

A variety of sequestrants or builders can be used in the present foaming composition, including, for example, organic phosphonate, aminocarboxylic acid, condensed phosphate, inorganic builder, polymeric polycarboxylate, mixture thereof, or the like. Such sequestrants and builders are commercially available. In an embodiment, the foaming composition includes about 5 to about 60 wt-%, about 5 to about 40 wt-%, or about 30 to about 50 wt-% sequestrant or builder. In an embodiment, the present foaming composition can include about 10 (e.g., 9) wt-%. The composition can include any of these ranges or amounts not modified by about.

In an embodiment, the foaming composition includes sequestrant or builder in an amount effective to provide a desired level of cleaning.

Polycarboxylates suitable for use as cleaning agents include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, and the like. Suitable polycarboxylates include polyacrylate.

In an embodiment, the present solid cleaning composition includes about 1 to about 40 wt-%, about 2 to about 30 wt-%, or about 5 to about 15 wt-% polycarboxylate. In an embodiment, the present solid cleaning composition can include about 7 wt-% polycarboxylate. In an embodiment, the present foaming composition can include about 25 wt-% polycarboxylate. The composition can include any of these ranges or amounts not modified by about. In an embodiment, the foaming composition includes polycarboxylate in an amount effective to provide a desired level of cleaning.

The builder can include an organic phosphonate, such as an organic-phosphonic acid and alkali metal salts thereof. Some examples of suitable organic phosphonates include:

1-hydroxyethane-1,1-diphosphonic acid: $CH_3C(OH)[PO(OH)_2]_2$;
aminotri(methylenephosphonic acid): $N[CH_2PO(OH)_2]_3$;
aminotri(methylenephosphonate), sodium salt

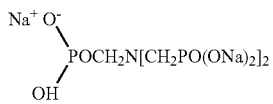

2-hydroxyethyliminobis(methylenephosphonic acid): $HOCH_2CH_2N[CH_2PO(OH)_2]_2$;
diethylenetriaminepenta(methylenephosphonic acid): $(HO)_2POCH_2N[CH_2CH_2N[CH_2PO(OH)_2]_2]_2$;
2-phosphonobutane-1,2,4-tricarboxylic acid;
diethylenetriaminepenta(methylenephosphonate), sodium salt: $C_9H_{(28-x)}N_3Na_xO_{15}P_5$ (x=7);
hexamethylenediamine(tetramethylenephosphonate), potassium salt: $C_{10}H_{(28-x)}N_2K_xO_{12}P_4$ (x=6);
bis(hexamethylene)triamine(pentamethylenephosphonic acid): $(HO_2)POCH_2N[(CH_2)_6N[CH_2PO(OH)_2]_2]_2$; and
phosphorus acid $H_3PO_3$; and other similar organic phosphonates, and mixtures thereof.

Suitable organic phosphonates include PBTC.

In an embodiment, the present solid cleaning composition includes about 0.1 to about 20 wt-%, about 0.5 to about 10 wt-%, or about 1 to about 5 wt-% phosphonate. In an embodiment, the present solid cleaning composition can include about 2 wt-% phosphonate. The composition can include any of these ranges or amounts not modified by about. In an embodiment, the foaming composition includes phosphonate in an amount effective to provide a desired level of cleaning.

The sequestrant can be or include aminocarboxylic acid type sequestrant. Suitable aminocarboxylic acid type sequestrants include the acids or alkali metal salts thereof, e.g., amino acetates and salts thereof. Some examples include the following:

N-hydroxyethylaminodiacetic acid;
hydroxyethylenediaminetetraacetic acid, nitrilotriacetic acid (NTA);
ethylenediaminetetraacetic acid (EDTA);
N-hydroxyethyl-ethylenediaminetriacetic acid (HEDTA);
diethylenetriaminepentaacetic acid (DTPA); and
alanine-N,N-diacetic acid;

and the like; and mixtures thereof.

Suitable aminocarboxylates include ethylenediamine tetraacetic acid (EDTA), diethylenetriamine pentaacetic acid (DTPA), their alkali metal salts, and mixtures thereof. Suitable aminocarboxylates include the sodium salt of EDTA.

Suitable condensed phosphates include sodium and potassium orthophosphate, sodium and potassium pyrophosphate, sodium and potassium tripolyphosphate, sodium hexametaphosphate, and the like, e.g., the sodium salt, e.g., of pyrophosphate. A condensed phosphate may also assist, to a limited extent, in solidification of the composition by fixing the free water present in the composition as water of hydration. In an embodiment, the present foaming composition includes as a builder, chelator, or sequestrant a condensed phosphate, such as tetrasodium pyrophosphate.

In an embodiment, the present foaming composition includes as sequestrant or builder condensed polyacrylate and phosphonate, for example, sodium polyacrylate and 2-phosphonobutane-1,2,4-tricarboxylic acid (PBTC, sold under the tradename Bayhibit AM).

Additives

The present composition can also include any number of additives. Additives and other additive ingredients will vary according to the type of composition being manufactured, and the intended end use of the composition. Examples of conventional additives include one or more of each of source of alkalinity, salt, detersive polymer, cleaning agent including cleaning enzyme, rinse aid composition, stabilizing agent, wetting agent, thickener, softener, pH modifier, source of acidity, anti-corrosion agent, solubility modifier, detergent filler, anti-redeposition agent, rinse aid composition, threshold agent or system, aesthetic enhancing agent (i.e., dye, odorant, perfume), enzyme, effervescent agent, other such additives or functional ingredients, and the like, and mixtures thereof. Such additives can be preformulated with the present composition or added to the system simultaneously, or even after, the addition of the present composition.

Source of Alkalinity

The present foaming composition can include effective amounts of one or more inorganic detergents or alkalinity sources to improve soil removal performance of the composition. The source of alkalinity can include an alkali metal salt, such as alkali metal carbonate, alkali metal hydroxide, alkali metal silicate (e.g., metasilicate), or the like; metal borate, such as sodium or potassium borate, and the like; ethanolamines and amines; inorganic alkalinity source, such as alkali metal hydroxide or silicate (e.g., metasilicate), or the like; and other like alkaline sources. In an embodiment, the quantity of alkalinity source is sufficient to render the composition strongly alkaline. In an embodiment the source of alkalinity includes sodium hydroxide, metal borate, alkali metal silicate, amine, or a mixture thereof.

Suitable alkali metal hydroxides include, for example, sodium or potassium hydroxide, in an embodiment sodium hydroxide. An alkali metal hydroxide may be added to the composition in a variety of forms, including for example in the form of solid beads, dissolved in an aqueous solution, or a combination thereof. Alkali metal hydroxides are commercially available as a solid in the form of prilled solids or beads having a mix of particle sizes ranging from about 12-100 U.S. mesh, or as an aqueous solution, as for example, as a 50 wt-% and a 73 wt-% solution.

Examples of useful alkaline metal silicates include sodium or potassium silicate (with a $M_2O:SiO_2$ ratio of 1:2.4 to 5:1, M representing an alkali metal) or metasilicate. Suitable alkaline metal silicates include sodium metasilicate.

In an embodiment, the present solid cleaning composition includes about 2 to about 7 wt-%, about 2.5 to about 6 wt-%, or about 3 to about 5 wt-% source of alkalinity. In an embodiment, the present foaming composition can include about 4 wt-% source of alkalinity. The composition can include any of these ranges or amounts not modified by about. In an embodiment, the foaming composition includes source of alkalinity in an amount effective to provide a desired level of cleaning.

Thickening or Gelling Agents

Suitable thickeners can include those which do not leave contaminating residue on the surface of food product or food product processing apparatus. That is, preferred thickeners or gelling agents do not include components incompatible with food or other sensitive products in contact areas. In addition, the thickeners should not inhibit the growth of the benign microbial component of the present foaming composition.

Generally, thickeners which may be used in the present invention include natural gums such as xanthan gum, guar gum, modified guar, or other gums from plant mucilage; polysaccharide based thickeners, such as alginates, starches, and cellulosic polymers (e.g., carboxymethyl cellulose, hydroxyethyl cellulose, and the like); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 3 wt-%, from about 0.1 wt-% to about 2 wt-%, or about 0.1 wt-% to about 0.5 wt-%.

Dyes and Fragrances

Various dyes, odorants including perfumes, and other aesthetic enhancing agents may also be included in the composition provided such dyes and/or fragrances do not adversely affect the growth and proliferation of the benign microbes of the present composition.

Dyes may be included to alter the appearance of the composition, as for example, any of a variety of FD&C dyes, D&C dyes, and the like. Additional suitable dyes include Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), Pylakor Acid Bright Red (Pylam), and the like.

Fragrances or perfumes that may be included in the compositions include, for example, a jasmine such as C1S-jasmine or jasmal, vanillin, and the like.

Embodiments of Compositions

The composition can be provided as a two-part or a three-part composition. In other words, the composition can be maintained as two or three separate components which are mixed prior to use of the compositions. For example, the first part of a two-part composition can include a surfactant blend while the second part can include a microbe.

Some examples of representative constituent concentrations for the surfactant part of a multi-part composition can be found in Table A, in which the values are given in wt-% of the ingredients in reference to the total weight of the surfactant part. In certain embodiments, the proportions and amounts in Table A can be modified by "about".

TABLE A

Compositional Ranges for Surfactant Blend of a Two-Part Composition

| Class of Ingredient | Exemplary Ingredients: | Wt-% | Wt-% | Wt-% | Wt-% |
|---|---|---|---|---|---|
| Surfactant | Nonionic, Anionic, and/or Amphoteric surfactants | 20-70 | 25-60 | 30-50 | 42 |
| Sequestrant | | 0.01-3 | 0.1-1 | 0.25-0.75 | 0.5 |
| Solvent | Water, Glycol | 10-90 | 30-80 | 40-70 | 57 |

The surfactant part of a multi-part composition can include anionic, nonionic, and/or amphoteric surfactants. Some exemplary representative constituent concentrations for the surfactant blend of the surfactant part are provided in Table B, in which the values are given in wt-% of the ingredients in reference to the total weight of the surfactant part. In certain embodiments, the proportions and amounts in Table B can be modified by "about".

TABLE B

Compositional Ranges for Surfactant Blend of Surfactant Part

| Class of Ingredient | The Class Includes: | Wt-% | Wt-% | Wt-% | Wt-% |
|---|---|---|---|---|---|
| Nonionic Surfactant | Amine oxide, Nonylphenol ethoxylate | 0.01-70 | 1-45 | 10-30 | 18 |
| Anionic Surfactant | Fatty alcohol ether sulfate, Sodium dioctyl Sulfosuccinate, Sodium xylene sulfonate | 0.01-70 | 1-45 | 10-30 | 18 |
| Amphoteric Surfactant | DEA coco amide | 0.1-40 | 0.5-25 | 2.5-10 | 5 |

Some examples of representative constituent concentrations for the sequestrant part of a multi-part composition can be found in Table C, in which the values are given in wt-% of the ingredients in reference to the total weight of the sequestrant part. The sequestrant is optional but can be employed when hard water will be present at the site of use of the composition or used in the composition. In certain embodiments, the proportions and amounts in Table C can be modified by "about".

TABLE C

Compositional Ranges for Sequestrant Part of Multi-Part Composition

| Class of Ingredient | The Class Includes: | Wt-% | Wt-% | Wt-% | Wt-% |
|---|---|---|---|---|---|
| Sequestrant/ Builder/ Chelator | Polyphosphates, Tripolyphosphates, Polymers | 1-70 | 5-55 | 15-40 | 25 |
| Solvent | Water | 5-95 | 15-95 | 35-85 | 75 |

Concentrate and Use Compositions, Foams, and Foaming

The compositions of the present invention can be formulated by combining the foaming component, the benign microbial component, and any other ingredients. For example, these ingredients can be mixed to form a concentrate or superconcentrate composition, which can be diluted at the site of use to form a use composition.

Superconcentrates do not include water as a purposefully added raw material (though water can be present in some of the ingredients). Superconcentrates can be formulated which are both flowable and stable and can be useful to provide small dispensed volumes or individual dosage packs.

The invention contemplates a concentrate composition which is diluted to a use solution prior to application to an object. Primarily for reasons of economics, the concentrate would normally be marketed and an end user would preferably dilute the concentrate with water or an aqueous diluent to a use solution. The foaming composition according to the present invention can be dissolved in water to form an intermediate or use composition. For example, at the site of use, a concentrate or intermediate concentration can be diluted to form the use composition. For example, the foaming composition can be diluted directly with water to form a use composition.

The level of active components in the concentrate composition is dependent on the intended dilution factor and the desired competitive exclusion activity of the foaming microbial composition. Generally, a dilution of about 0.1 to about 25 ounces of concentrate composition per gallon of diluent (e.g., water) provides a suitable use composition. In the typical use locus, the concentrate is diluted with a major proportion of water using commonly available tap or service water.

The foaming composition can be provided as a single or as a 2-part composition. For example, a first part of a 2-part composition can include those components that unacceptably degrade viability of the microbe. For example, a second part of a 2-part composition can include those components compatible with acceptable viability of the microbe. A second part can include the microbial component. A second part can include the microbial component and the foaming component. A first part can include a source of alkalinity, a sequestrant, or the like.

The foaming component can provide foaming action through either a mechanical or chemical mechanism. For chemical foaming, the foaming component can include ingredients that create foam as a result of a chemical interaction, either with other ingredients in the composition, or with substances present in the applicable environment. These components can be provided as a 2-part composition that can be combined when foaming is desired.

In an embodiment, the present foaming composition can be dissolved to form a use composition that is used in a foamer. Foaming application can be accomplished, for example, using a foam application device such as a tank roamer or an aspirated wall mounted foamer, e.g., employing a foamer nozzle of a trigger sprayer. Foaming application can be accomplished by placing the use composition in a fifteen gallon foam application pressure vessel, such as a fifteen gallon capacity stainless steel pressure vessel with mix propeller. The foaming composition can then be dispensed through a foaming trigger sprayer. A wall mounted foamer can use air to expel foam from a tank or line.

In an embodiment, an object in a food processing environment can be treated with the present foaming composition. The foam can be prepared by mixing foaming surfactants with the benign microbes at the time or point of use. At time of use, compressed air can be injected into the mixture, then applied to the object through a foam application device such as a tank roamer or an aspirated wall mounted foamer.

Mechanical foaming heads that can be used according to the invention to provide foam generation include those heads that cause air and the foaming composition to mix and create a foamed composition. That is, the mechanical foaming head causes air and the foaming composition to mix in a mixing chamber and then pass through an opening to create a foam.

Suitable mechanical foaming heads that can be used according to the invention include those available from Airspray International, Inc. of Pompano Beach, Fla., and from Zeller Plastik, a division of Crown Cork and Seal Co. Suitable mechanical foaming heads that can be used according to the invention are described in, for example, U.S. Pat. No. D-452,822; U.S. Pat. No. D-452,653; U.S. Pat. No. D-456,260; and U.S. Pat. No. 6,053,364. Mechanical foaming heads that can be used according to the invention includes those heads that are actuated or intended to be actuated by application of finger pressure to a trigger that causes the foaming composition and air to mix and create a foam. That is, a person's finger pressure can cause the trigger to depress thereby drawing the foaming composition and air into the head and causing the foaming composition and air to mix and create a foam.

The use composition can include about 0.01 to about 3 wt-%, about 0.1 to about 2.5 wt-%, about 0.3 to about 2 wt-%, about 0.05 to about 2 wt-%, or about 0.1 to about 1.5 wt-% of the foaming composition.

Foam

When the present composition is provided as a foam, the composition has a cellular structure that can be characterized as having several layers of air cells that provide the composition with a foamy appearance. It should be understood that the characterization of a foam refers to the existence of more than simply a few air bubbles. In general, a foam can be characterized as having at least 50 wt-% foam using a 15 second vertical separation test. The test is carried out by spraying the foaming composition as a foam onto a vertical surface such as glass, waiting 15 seconds after application of the foam to the vertical surface, and then taking up the liquid portion and the foam portion in separate preweighted paper towels. The weight of the absorbed liquid can be calculated and the weight of the absorbed foam can be calculated. By providing a separation time of at least 15 seconds, it is believed that a reasonable amount of separation of liquid and foam can be achieved. The towel picking up the liquid portion should not pick up any of the foam portion, and the towel picking up the foam portion should not pick up the liquid portion that has fallen below the foam portion. It is understood that the foam portion may still include a small amount of associated liquid. However, this associated liquid is considered a part of the foam as long as it remains with the foam at the 15 second cut off time. The weight percent foam can be calculated by dividing the weight of the foam component by the total weight and multiplying by 100. The 15 second vertical separation test can be referred to as a "gravimetric foam test after 15 seconds." The foaming composition preferably provides at least 70 wt-% foam according to the gravimetric foam test after 15 seconds, more preferably at least about 90 wt-% foam, and even more preferably at least about 95 wt-% foam.

In general, it is desirable to have the foam hang up and not fall down a vertical surface to provide desired contact time and to allow the microbial component to disperse and better penetrate the surface being treated. The period of 15 seconds is selected for the test because it is expected that a foam will likely "hang" for at least about 15 seconds and any free liquid, if present at all, will have an opportunity to separate from the foam and fall down the vertical surface. In addition, the foam persists for at least about 15 seconds after application to a surface. This means that the foam will have a tendency to remain as a foam and will resist condensing to a liquid in order to provide the above-identified weight percent foam. More preferably, the foam persists for at least about 1 minute after application to the surface.

A cylinder foam test has been used in the surfactant industry to evaluate the foamability of test compositions. In general, a cylinder foam test can be carried out by charging a test composition into a stoppered, graduated cylinder so that the charge composition occupies about ⅓ to about ½ of the height of the stoppered, graduated cylinder. The stoppered, graduated cylinder can be inverted about 10 times and the height of foam generated can be recorded.

Methods Employing the Present Compositions

The compositions of the invention can be used for a variety of domestic or industrial applications, e.g., to reduce undesirable or pathogenic microbial or viral populations on a surface or object. The compositions can be applied in a variety of areas including kitchens, bathrooms, factories, hospitals, butcheries, or food plants, and can be applied to a variety of hard or soft surfaces having smooth, irregular or porous topography. Suitable hard surfaces include, for example, architectural surfaces (e.g., floors, walls, windows, sinks, drains, tables, counters, and signs). Such hard surfaces can be made from a variety of materials including, for example, ceramic, metal, glass, wood or hard plastic.

The present compositions can be employed for reducing the population of pathogenic microbes, such as pathogens of humans, animals, and the like, and/or for reducing the population of spoilage microbes. The compositions can exhibit activity against pathogens including fungi, molds, bacteria, spores, and viruses, for example, *Escherichia coli*, *Salmonella*, *Listeria* (e.g., *Listeria monocytogenes*), *Staphylococcus* (e.g., *S. aureus*), *Streptococcus*, *Bacillus anthracis*, *Campylobacter coli*, *Campylobacter jejuni*, *Francisella tularensis*, *Sarcocystis*, *Toxoplasma gondii*, *Yersinia enterocolitica*, *Yersinia pseudotuberculosis*, *Brucella*, *Chlamydia petechia*, *Leptospira*, *Clostridium*, *Legionella*, *Pseudomonas aeruginosa*, mycobacteria, or the like. The compositions can exhibit activity against spoilage microbes including bacteria from the genera *Pseudomonades*, *Lactobacillus*, and *Enterobacter*; molds from the genera *Aspergillus* and *Penicillium*; and yeasts from the genera *Saccharomyces* and *Candida*.

The compositions of the present invention can reduce the population of undesirable microbes on manufacturing or processing sites handling foods. The compositions of the present invention can be used on any surface at a food processing site that serves, or potentially could serve, as a source of contamination. For example, the compositions can be used on food transport lines (e.g., as belt sprays); boot and hand-wash dip-pans; food storage facilities; anti-spoilage air circulation systems; refrigeration and cooler equipment; plumbing, and floor drains. The present compositions can also be used on or in other industrial equipment such as heaters, cooling towers, boilers, and the like. The present compositions can also be used on or in wash tanks, soaking vessels, mop buckets, holding tanks, scrub sinks, vehicle parts washers, non-continuous batch washers and systems, and the like.

The composition can be employed by dipping food processing or other equipment into the use solution, soaking the equipment for a time sufficient to inoculate the equipment with the benign microbe, and wiping or draining excess solution off the equipment. The composition may be further employed by spraying or wiping food processing surfaces with the use solution, keeping the surfaces wet for a time sufficient to inoculate the surface with the benign microbe, and removing excess solution by wiping, draining vertically, vacuuming, etc.

A foaming composition of the present invention can be applied to or brought into contact with an object by any conventional method or apparatus for applying a foaming composition to an object. For example, the object can be wiped with, sprayed with, and/or immersed in the foaming composition, or a use solution made from the foaming composition. The composition can be sprayed or wiped onto a surface; the composition can be caused to flow over the surface, or the surface can be dipped into the foaming composition. Contacting can be manual or by machine.

The present invention may be better understood with reference to the following examples. These examples are intended to be representative of specific embodiments of the invention, and are not intended as limiting the scope of the invention.

Examples

Some exemplary compositions were prepared and tested in the drains of a food processing plant to determine the ability of the microbial component to grow and proliferate on the surface being treated.

Viability of Microorganisms in Concentrate Compositions

Diluted aliquots of microorganisms were mixed with a foaming composition or a surfactant blend. The populations of *Enterococcus durans* 152 and *Lactococcus lactis* C-1-92 were then analyzed immediately, after 24 hours, and after four days. The following results were observed.

| | Alkyl Poly Glycoside (10% in water, neutralized with $H_3PO_4$, pH 6.9) | | |
|---|---|---|---|
| Composition 1 | Immediate | 24 Hours | 4 Days |
| *Enterococcus durans* | $4.70 \times 10^6$ | $5.00 \times 10^6$ | $2.3 \times 10^6$ |
| *Lactococcus lactis* | $1.60 \times 10^7$ | $3.90 \times 10^5$ | 0 |

| | 1% of Composition 1 in water (neutralized with $H_3PO_4$, pH 7.04) | | |
|---|---|---|---|
| Composition 2 | Immediate | 24 Hours | 4 Days |
| *Enterococcus durans* | $5.90 \times 10^6$ | $6.00 \times 10^6$ | $1.60 \times 10^6$ |
| *Lactococcus lactis* | $5.30 \times 10^6$ | $1.80 \times 10^2$ | 0 |

| | 10% Amphoteric Surfactant (pH 8.4) | | |
|---|---|---|---|
| Composition 3 | Immediate | 24 Hours | 4 Days |
| *Enterococcus durans* | $7.50 \times 10^6$ | $6.20 \times 10^6$ | $4.40 \times 10^6$ |
| *Lactococcus lactis* | $1.40 \times 10^7$ | $1.46 \times 10^7$ | $8.90 \times 10^4$ |

| | 1% Composition of Table B (right-most column) (pH 7.89) | | |
|---|---|---|---|
| Composition 4 | Immediate | 24 Hours | 4 Days |
| *Enterococcus durans* | $5.70 \times 10^6$ | $4.30 \times 10^6$ | $3.60 \times 10^5$ |
| *Lactococcus lactis* | $8.10 \times 10^6$ | $5.90 \times 10^4$ | $3.50 \times 10^2$ |

Compositions 3 and 4 provided adequate maintenance of viability of each microbe in the concentrate compositions.

Applying Compositions to Drains

Test 1

The microbial component of the exemplary compositions was prepared by inoculating three liters of MRS Broth with *Enterococcus durans* 152, and incubating for about 24 hours at about 32° C. The resulting culture was centrifuged to yield pellets which were resuspended in 300 mL of MRS Broth. The resulting product was packaged into 25 mL aliquots. This same procedure was followed using *Lactococcus lactis* C-1-92. Aliquots of each benign microbe were diluted in water.

An exemplary composition was tested to analyze its ability to competitively exclude *Listeria monocytogenes*, an undesirable microbe. The exemplary composition was prepared by mixing 40 mLs each of the high foaming composition sold under the tradename Dy-gest I™ (Table B, right-most column) and the sequestrant composition sold under the tradename Dy-gest II™ (Table C, right most column) (both available from Klenzade®, a service of Ecolab, Inc.) into one gallon of tap water. 25 mL aliquots of both microbes were added to a spray tank. Thereafter, the mixture of the high foaming composition and the alkaline cleaning composition was also added to the spray tank.

The resulting use composition included (in wt-% or ppm) the following components:

one through four of week zero and then periodically (approximately weekly) until the second day of week 7.

The drains were sampled for *Listeria* by swabbing four different locations in each drain. The swabs were cultured and then number of swabs that contained *Listeria* were counted and reported in Table 1. If all four swabs contained *Listeria*, the entry in the Table is 4. The samples taken before application of the present compositions represent pre-treatment levels of *Listeria*. The sample taken in week zero was taken the last day of week zero.

TABLE 1

Number of Swabs Containing Listeria

| | Week Drain | | | | | | | | | |
|---|---|---|---|---|---|---|---|---|---|---|
| | −11 | −7 | −2 | 0 | 3 | 8 | 10 | 13 | 16 | 20 |
| Untreated 1 | 3 | 2 | 2 | 0 | 1 | 3 | 2 | 1 | 3 | 4 |
| Untreated 2 | 0 | 3 | 2 | 1 | 1 | 0 | 2 | 0 | 4 | 2 |
| Treated 1 | 3 | 4 | 2 | 1 | 0 | 0 | 0 | 0 | 0 | 0 |
| Treated 2 | 4 | 2 | 3 | 0 | 0 | 0 | 0 | 0 | 2 | 1 |
| Treated 3 | 3 | 2 | 4 | 0 | 0 | 0 | 0 | 0 | 0 | 0 |
| Treated 4 | 4 | 2 | 3 | 0 | 0 | 0 | 0 | 0 | 2 | 0 |
| Treated 5 | 3 | 3 | 3 | 0 | 0 | 0 | 0 | 0 | 0 | 0 |
| Treated 6 | 1 | 3 | 3 | 0 | 1 | 3 | 1 | 0 | 3 | 0 |

| Class of Ingredient | The Class Includes: | Wt-% | Wt-% | Wt-% | Wt-% |
|---|---|---|---|---|---|
| Nonionic Surfactant | Amine oxide, Nonylphenol ethoxylate | 0.0025-5.0 | 0.01-0.2 | 0.05-0.15 | 0.1 |
| Anionic Surfactant | Fatty alcohol ether sulfate, Sodium dioctyl Sulfosuccinate, Sodium xylene sulfonate | 0.0025-5 | 0.01-0.2 | 0.05-0.15 | 0.1 |
| Amphoteric Surfactant | DEA coco amide | 0.0125-5 | 0.05-1.0 | 0.25-0.75 | 0.5 |
| Source of Alkalinity | Sodium tetraborate, Sodium carbonate | 0.00-0.1 | 0.001-0.06 | 0.015-0.045 | 0.03 |
| Sequestrant/Builder/ Chelator | Polyphosphates, Tripolyphosphates, Polymers | 0.000-0.5 | 0.01-0.2 | 0.05-0.15 | 0.1 |
| *Enterococcus durans* | *Enterococcus* sp. | $10^1$-$10^{15}$ | $10^2$-$10^{12}$ | $10^3$-$10^9$ | $10^6$ |
| *Lactococcus lactis* | *Lactococcus* sp. | $10^1$-$10^{15}$ | $10^2$-$10^{12}$ | $10^3$-$10^9$ | $10^6$ |

The spray tank was gently shaken to mix the bacteria and foaming/cleaning compositions. The population of *Listeria monocytogenes* in each of the drains used in the experiment were analyzed over the course of about two and a half months without treatment. Thereafter the composition was applied to each drain once every day for four days followed by twice per week for four weeks, with two of the drains used as controls. The population of *Listeria monocytogenes* was analyzed at regular intervals.

The results observed are illustrated by the graph shown in FIG. 1.

Test 2

The same compositions employed in Test 1 were applied to several drains in a plant producing ready to eat foods. The untreated drains received no composition (no treatment). The competitive exclusion compositions were applied on the days These results demonstrate that the treatment of the drains with the present competitive exclusion compositions significantly reduced the population *Listeria* in the treated drains. The number of swabs testing positive for *Listeria* seemed to increase about 16-20 weeks after treatment. This suggests that regular and continuing treatment with the competitive exclusion compositions can be advantageous.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured"

describes a system, apparatus, or other structure that is constructed or configured to perform a particular task or adopt a particular configuration. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A foamed composition comprising:
   about 0.01 to about 10 wt-% of foaming surfactant comprising nonionic surfactant, anionic surfactant, and amphoteric surfactant, the amphoteric surfactant selected from the group consisting of acyl amino acid, N-alkyl amino acid, salt or ester thereof, and mixtures thereof;
   about 0.05 to about 5 wt-% of a suspension comprising at least about $10^3$ colony forming units (CFU)/ml of bacteria from the genus *Enterococcus, Lactococcus, Hafnia*, or mixture thereof;
   and about 0.01-0.2 wt % of an ingredient selected from the group consisting of a sequestrant, builder, chelator, and mixtures thereof;
   wherein the composition comprises foam;
   the foamed composition being effective for reducing the population of an undesired microbe on a food processing surface.

2. The composition of claim 1, wherein the bacteria comprises *Enterococcus durans, Lactococcus lactis, Hafnia alvei*, or mixture thereof.

3. The composition of claim 1, wherein the nonionic surfactant comprises amine oxide, nonylphenol ethoxylate, or mixture thereof.

4. The composition of claim 1, wherein the anionic surfactant comprises fatty alcohol ether sulfate, sodium dioctyl sulfosuccinate, sodium xylene sulfonate, or mixture thereof.

5. The composition of claim 1, wherein the surfactant comprises alkanolamide.

6. The composition of claim 1, wherein the surfactant is selected to maintain at least 2% of the bacteria viable 24 hours after foaming.

7. The composition of claim 1, wherein the composition is of pH about 3 to about 10.

8. The composition of claim 2, wherein the bacterial component comprises bacteria from the genus *Hafnia*, which comprise *Hafnia alvei*; and the bacterial component further comprises *Lactobacillus delbrueckii*.

9. The composition of claim 1, wherein the foamed composition is effective for reducing the population of an undesired microbe on a drain surface.

* * * * *

UNITED STATES PATENT AND TRADEMARK OFFICE
CERTIFICATE OF CORRECTION

PATENT NO.       : 7,795,000 B2
APPLICATION NO.  : 11/233922
DATED            : September 14, 2010
INVENTOR(S)      : Podtburg et al.

Page 1 of 1

It is certified that error appears in the above-identified patent and that said Letters Patent is hereby corrected as shown below:

Front page, (54) Title: "AND METHODS OF USING SAME" should read --AND METHOD OF USING SAME--

Col. 1, line 3: "AND METHODS OF USING SAME" should read --AND METHOD OF USING SAME--

Signed and Sealed this
Twenty-fourth Day of May, 2011

David J. Kappos
*Director of the United States Patent and Trademark Office*